United States Patent [19]

Breuer et al.

[11] 4,100,345
[45] Jul. 11, 1978

[54] 3-(CARBAMOYL)PYRIDINO DERIVATIVES OF 7A-METHOXY UREIDOCEPHALOSPORINS

[75] Inventors: Hermann Breuer; Uwe D. Treuner, both of Regensburg, Fed. Rep. of Germany

[73] Assignee: E. R. Squibb & Sons, Inc., Princeton, N.J.

[21] Appl. No.: 761,914

[22] Filed: Jan. 24, 1977

Related U.S. Application Data

[62] Division of Ser. No. 664,335, Mar. 5, 1976, Pat. No. 4,024,135.

[51] Int. Cl.² .................. C07D 501/40; C07D 501/44
[52] U.S. Cl. .................................................. 544/21
[58] Field of Search ........................ 260/243 C; 544/21

[56] References Cited

U.S. PATENT DOCUMENTS

| 3,994,886 | 11/1976 | Crooij et al. | 260/243 C |
| 3,996,218 | 12/1976 | Breuer et al. | 260/243 C |
| 4,000,134 | 12/1976 | Dolfini | 260/243 C |
| 4,029,653 | 6/1977 | Dolfini | 260/243 C |

Primary Examiner—Donald G. Daus
Assistant Examiner—David E. Wheeler
Attorney, Agent, or Firm—Lawrence S. Levinson; Merle J. Smith; Stephen B. Davis

[57] ABSTRACT

Ureido cephalosporin derivatives of the formula

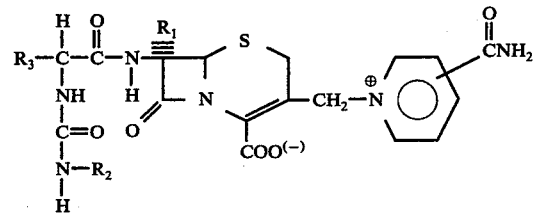

wherein $R_1$ is hydrogen or methoxy; $R_2$ is hydrogen or lower alkyl; $R_3$ is hydrogen, lower alkyl, cycloalkyl, cycloalkenyl, cycloalkadienyl, phenyl, phenyl-lower alkyl, substituted phenyl, substituted phenyl-lower alkyl; or certain heterocyclic groups; are disclosed. These compounds are useful as antibacterial agents.

18 Claims, No Drawings

3-(CARBAMOYL)PYRIDINO DERIVATIVES OF 7A-METHOXY UREIDOCEPHALOSPORINS

This is a division, of application Ser. No. 664,335, filed on Mar. 5, 1976 and now U.S. Pat. No. 4,024,135.

BACKGROUND OF THE INVENTION

Cephalosporins having a carbamoyl substituted pyridinomethyl group in the 3-position are disclosed in U.S. Pat. Nos. including 3,261,832; 3,449,338; 3,479,350; 3,483,197; 3,557,104; 3,632,810; etc.; and German Offenlegungsschrift No. 2,234,280.

Cephalosporins having a ureido acyl side chain are disclosed in U.S. Pat. Nos. 3,673,183; 3,708,479; 3,833,568; and 3,860,591. Cephalosporins having various acyl side chains and a 7α-methoxy substituent are taught in various U.S. Pat. Nos. including 3,775,410; 3,780,031; 3,780,033; 3,780,034; 3,780,037; 3,843,641; etc.

Cephalosporins having an acylureido acyl side chain are disclosed in U.S. Pat. Nos. 3,687,949 and 3,925,368 and German Offenlegungsschrift Nos. 2,513,954 and 2,514,019.

SUMMARY OF THE INVENTION

This invention relates to new carbamoyl substituted pyridinomethyl ureiodcephalosporins of the formula $$\text{(I)}$$

$R_1$ represents hydrogen or methoxy. The $R_1$ substituent is in the α-configuration as indicated by the broken lines (≡).

$R_2$ represents hydrogen or lower alkyl.

$R_3$ represents hydrogen, lower alkyl, cycloalkyl, cycloalkenyl, cycloalkadienyl, phenyl, phenyl-lower alkyl, substituted phenyl, substituted phenyl-lower alkyl, or certain heterocyclic groups.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbon groups containing 1 to 8 carbon atoms, preferably 1 to 4 carbons. Examples of the type of groups contemplated are methyl, ethyl, propyl, isopropyl, butyl, t-butyl, etc. The lower alkoxy groups include such lower alkyl groups attached to an oxygen, e.g., methoxy, ethoxy, propoxy, etc. The phenyllower alkyl groups include such lower alkyl groups attached to a phenyl, preferably benzyl and phenethyl.

Cycloalkyl refers to groups having 3 to 7 carbons in the ring, i.e. cyclopropyl, cyclobutyl, cycopentyl, cyclohexyl, and cycloheptyl. The term cycloalkenyl also represent rings having 3 to 7 carbons with one double bond, i.e. cyclobutenyl, cyclopentenyl, cyclohexenyl, etc. The term cycloalkadienyl represents a ring having 6 or 7 carbons with two double bonds located at various positions such as 1,4-cyclohexadienyl which is preferred.

The substituted phenyl and substituted phenyl-lowr alkyl groups include one or two substituents selected from halogen (preferably chlorine or bromine), lower alkyl of 1 to 4 carbons (preferably methyl or ethyl), lower alkoxy of 1 to 4 carbons (preferably methoxy or ethoxy), and hydroxy, e.g. 2-, 3-, or 4-chlorophenyl, 2-, 3-, or 4-bromobenzyl, 2-, 3-, or 4-hydroxyphenyl, 3,5-dichlorophenyl, 2-, 3-, or 4-methylphenyl, 2-, 3-, or 4-ethoxyphenyl, etc.

The heterocyclic groups represented by $R_3$ are 2-thienyl, 3-thienyl, 2-furyl, 3-furyl, 2-pyridyl, 3-pyridyl, or 4-pyridyl. Also included within the meaning of $R_3$ are such heterocyclics having a halogen (preferably Cl or Br) or a lower alkyl of 1-4 carbons (preferably methyl or ethyl) substituent, i.e. 2-(4-chlorothienyl), 3-(4-methylthienyl), etc.

The compounds of formula I can be prepared by several methods. The preferred method is by reacting a compound of the formula $$\text{(II)}$$

or its sodium salt with a carbamoyl substituted pyridine in a polar solvent such as water and in the presence of a catalyst such as an alkali metal thiocyanate.

The compounds of formula II can be obtained by acylating an α-ureido compound of the formula $$\text{(III)}$$

with a 7-ACA or 7α-methoxy-7-ACA of the formula $$\text{(IV)}$$

wherein R is preferably diphenylmethyl or another ester protecting group. The resulting product is then treated to remove the ester group such as by the use of anisole and trifluoroacetic acid to yield the compound of formula II.

In this reaction, the α-ureido compound of formula III must first be converted into an activated form. For example, the α-ureido compound of formula III can be converted to a mixed carbonic or other anhydride by treating a solution of the α-ureido compound in an organic solvent containing a tri(lower alkyl)amine with an anhydride forming agent, i.e. a lower alkyl chloroformate, an aryl chloroformate, or an acyl halide, at reduced temperatures of from about 0° C to about −20°

C. Alternatively, the α-ureido compound of formula III can be converted to an activated ester by reacting with a carboxyl group activating agent such as dicyclohexylcarbodiimide or bisimidazole carbonyl. In some cases the carboxyl group may be activated by conversion to an acid halide, e.g. the chloride, or to an azide. The methods of preparing the α-ureido compounds of formula III are known to those skilled in the art and a number of such methods are discussed in U.S. Pat. Nos. 3,673,183 and 3,833,568 referred to above.

Alternatively, the compounds of formula I can also be obtained by reacting an α-amino intermediate of the formula

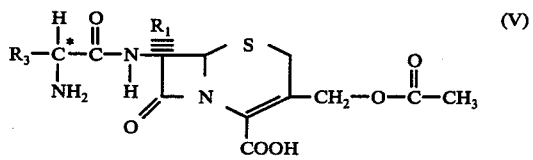
(V)

preferably in the form of its trifloroacetic acid salt with an isocyanate of the formula

(VI)

wherein $R_2$ is hydrogen, lower alkyl or an alkali or alkaline earth salt such as potassium. Also, the intermediate of formula V can be reacted with a compound of the formula

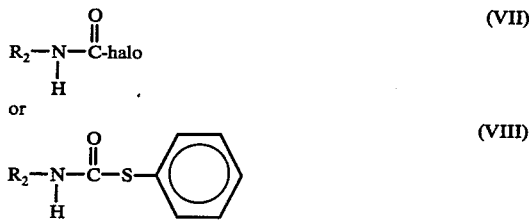
(VII)

(VIII)

wherein $R_2$ is as defined above and halo is Cl or Br.

The α-amino intermediate of formula V can be obtained by various methods such as by acylating the compound of formula IV with a substituted α-amino acid of the formula

(IX)

wherein Y is a protecting group such as

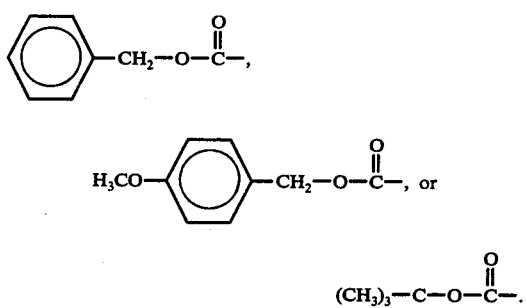

The α-amino protecting group is then removed by treating the resulting cephalosporin with trifluoroacetic acid and anisole.

Alternatively, the final compounds of formula I can be obtained by reacting the intermediate of formula V with a carbamoyl substituted pyridine followed by reaction with a compound of formula VI, VII, or VIII.

Also, the final compounds of formula I can be obtained by reacting the starting material of formula IV with a carbamoyl substituted pyridine followed by an acylation reaction with an activated form of the α-ureido compound of formula III.

It will be appreciated that the compounds of formula I are optically active due to the presence of an asymmetric carbon atom represented as C* in the preceding formulas. By selection of the appropriate starting material it is possible to obtain the compounds of formula I as a mixture of optically active isomers or isolated as a single isomer. The various isomers as well as their mixtures are within the scope of this invention.

Preferred compounds of this invention are those of formula I wherein $R_3$ is cyclohexenyl, cyclohexadienyl, phenyl, benzyl, phenethyl, substituted phenyl, benzyl, or phenethyl wherein the substituent is on the phenyl ring and is one or two members selected from chloro, bromo, methyl, ethyl, methoxy, ethoxy and hydroxy, or a substituted or unsubstituted heterocyclic selected from 2-thienyl, 3-thienyl, 2-furyl, 3-furyl, 2-pyridyl, 3-pyridyl and 4-pyridyl wherein the heterocyclic substituent is chloro, bromo, methyl, or ethyl and $R_2$ is hydrogen or straight or branched chain alkyl of 1 to 4 carbons.

The most preferred final compounds are those of formula I wherein the carbamoyl substituent is that 4-position and $R_4$ is 2-thienyl, 3-thienyl, phenyl, or 4-hydroxyphenyl.

The compounds of formula I have a broad spectrum of antibacterial activity against both gram positive and gram negative organisms such as *Staphylococcus aureus, Salmonella schottmuelleri, Pseudomonas aeruginosa, Proteus rettgeri, Escherichia coli, Klebsiella pneumoniae, Serratia marcescens*, etc. They may be used as antibacterial agents in a phophylactic manner, e.g, in cleaning or as surface disinfecting compositions, or otherwise to combat infections due to organisms such as those named above, and in general may be utilized in a manner similar to cephalothin and other cephalosporins. For example, a compound of formula I or a physiologically acceptable salt thereof may be used in various animal species in an amount of about 1 to 100 mg./kg., daily, orally or parenterally, in single or two to four divided doses to treat infections of bacterial origin, e.g., 5.0 mg./kg. in mice.

Up to about 600 mg. of an acid compound of formula I or a physiologically accceptable salt thereof may be incorporated in an oral dosage form such as tablets, capsules or elixirs or in an injectable form in a sterile aqueous vehicle prepared according to conventional pharmaceutical practice.

They may also be used in cleaning or disinfecting compositions, e.g., for cleaning barns or dairy equipment, at a concentration of about 0.2 to 1% by weight of such compounds admixed with, suspended or dissolved in conventional inert dry or aqueous carriers for application by washing or spraying.

They are also useful as nutritional supplements in animal feeds.

Illustrative process details are provided in the examples for the various reactions. All temperatures are on the centigrade scale.

EXAMPLE 1

7β-[[D-[(Aminocarbonyl)amino]-2-thienylacetyl]amino]-3-[[4-(aminocarbonyl)pyridino]methyl]-8-oxo-5-thia-1-azabicyclo-[4.2.0]oct-2-ene-2-carboxylic acid (a) D-2-[[[(4-Methoxyphenyl)methoxy]carbonyl]amino]-2-thiopheneacetic acid 74 g. of D-2-Thienylglycine are dissolved in 940 ml. of water. 37.8 g. of magnesium oxide are added and to this resulting suspension a solution of 107.5 g. of p-methoxybenzyloxycarbonylazide in 940 ml. of dioxane is added with stirring. The mixture is stirred at room temperature for 24 hours. It is then filtered and the filtrate is extracted with 600 ml. of ether. The extract is discarded. The water in dioxane phase is layered over with 600 ml. of ethyl acetate, cooled to 5° and brought to pH 2 with 2N hydrochloric acid. The layers are separated and the aqueous layer is again extracted with 300 ml. of ethyl acetate. The combined ethyl acetate extracts are washed with water, dried with magnesium sulfate, filtered and concentrated. The oily residue crystallizes upon trituration with petroleum ether to yield 118 g. of D-2-[[[(4-methoxyphenyl)methoxy]carbonyl]amino]-2-thiopheneacetic acid; m.p. 84°–94°; $[\alpha]^D_{20}$: −69° (c=1, tetrahydrofuran).

(b) 3-[(Acetyloxy)methyl-7β-[[D-[[[(4-methoxyphenyl)methoxy]-carbonyl]amino]-2-thienylacetyl]amino]-8-oxo-5-thia-1-azabicyclo[4.2.0]oct-2-ene-2-carboxylic acid 3.2 g. (0.01 mole) of the D-2-[[[(4-methoxyphenyl)methoxy]carbonyl]amino]-2-thiopheneacetic acid from part (a) are brought into solution in 40 ml. of methylene chloride with 1.1 ml. of N-methylmorpholine. The solution is cooled to −15°, 1.39 ml. of isobutylchloroformate are added, and the mixture is stirred for 10 minutes. To this is added a solution of 3.26 g. (0.1012 mol.) of 7-aminocephalosporanic acid and 3.1 ml. of triethylamine in 40 ml. of methylene chloride. The mixture is stirred for 1 hour at −5° and 1 hour at 5°. This mixture is then evaporated to dryness in a rotary evaporator. The solid residue is triturated with ether and filtered under suction. The substance is then dissolved in ice water, layered over with ethyl acetate and acidified to pH 2.5. The layers are separated, the aqueous layer is extracted once more with ethyl acetate, the combined ethyl acetate extracts are washed with water, dried with magnesium sulfate and concentrated. The residue (4.9 g.) is dissolved in 200 ml. of ethyl acetate and the solution is treated with activated carbon. After filtration, 2 g. of 3-[(acetyloxy)methyl]-7β-[[D-[[[(4-methoxyphenyl)methoxy]carbonyl]amino]-2-thienylacetyl]amino]-8-oxo-5-thia-1-azabicyclo[4.2.0]oct-2-ene-2-carboxylic acid, crystallize; m.p. 142°–143° (dec.).

(c) 3-[(Acetyloxy)methyl]-7β-[D-2-amino-2-(2-thienyl)acetamido]-8-oxo-5-thia-1-azabicyclo[4.2.0]oct-2-ene-2-carboxylic acid 2.0 g. of the product from part (b) are added at −5° to a mixture of 10 ml of trifluoroacetic acid and 4 ml. of anisole. The mixture is stirred for 15 minutes and is then concentrated in a rotary evaporator. The residue is treated with ether and filtered under suction. The crude 3-[(acetyloxy)methyl]-7β-[D-2-amino-2-(2-thienyl)acetamido]-8-oxo-5-thia-1-azabicyclo[4.2.0]oct-2-ene-2-carboxylic acid, trifluoroacetic acid salt is dissolved in 50 ml. of water and 20 ml. of a solution of the acetate form of the ion exchange resin Amberlite LA 1 in isobutylmethyl ketone are added. The mixture is stirred for 2 hours at room temperature. The layers are separated, the aqueous phase is washed several times with ether and freeze-dried to yield 3-[(acetyloxy)methyl]-7β[D-2-amino-2-(2-thienyl)acetamido]-8-oxo-5-thia-1-azabicyclo-[4.2.0]oct-2-ene-2-carboxylic acid.

(d) 3-[(Acetyloxy)methyl]-7β-[[D-[(aminocarbonyl)amino]-2-thienylacetyl]amino]-8-oxo-5-thia-1- azabicyclo[4.2.0]-oct-2-ene-2-carboxylic acid, sodium salt A mixture of 1 g. of the product from part (c) and 0.194 g. of potassium cyanate in 7.5 ml. of water are quickly heated in a preheated bath at 80°. The mixture is then immediately cooled to room temperature and permitted to stand overnight. The reaction mixture is concentrated to about 4 ml. and the pH is adjusted to 1.5 with 2N hydrochloric acid. The precipitate is filtered under suction to obtain 3-[(acetyloxy)methyl]-7β-[[D-[(aminocarbonyl)amino]-2-thienylacetyl]amino]-8-oxo-5-thia-1-azabicyclo[4.2.0]oct-2-ene-2-carboxylic acid.

An aqueous equimolar mixture of this acid and sodium bicarbonate is lyophilized to yield 3-[(acetyloxy)methyl]-7β-[[D-[(aminocarbonyl)amino]-2-thienylacetyl]amino]-8-oxo-5-thia-1-azabicyclo[4.2.-0]oct-2-ene-2-carboxylic acid, sodium salt.

(e) 7β-[[D-[(Aminocarbonyl)amino]-2-thienylacetyl]amino]-3-[[4-(aminocarbonyl)pyridino]methyl]-8-oxo-5-thia-1-azabicyclo[4.2.0]oct-2-ene-2-carboxylic acid A mixture of 2.38 g. (0.005 mole) of the sodium salt product from part (d), 0.915 (0.0075 mole) of 4-pyridinecarboxamide, 12 g. of potassium thiocyanate and 7.5 ml. of water is heated at 50° for 24 hours. A clear solution is obtained.

A chromatography column is filled with 150 g. of ion exchange resin Amberlite XAD-2. An additional 150 g. are made into a paste with a little water and added to the above reaction solution. This solution is stirred for 30 minutes and then added to the chromatography column containing the 150 g. of resin. The column is eluted with 30 ml. portions of water. After 120 fractions which are discarded, the column is eluted with a mixture of water and methanol (80:20) and fractions of 10 ml. each are collected. Fractions 47-120 are concentrated to about 150 ml. and freeze-dried. The residue is triturated with ether to obtain 0.7 g. of 7β-[[D-[(aminocarbonyl)amino]-2-thienylacetyl]amino]-3-[[4-(aminocarbonyl)-pyridino]methyl]-8-oxo-5-thia-1-azabicyclo-[4.2.0]oct-2-ene-2-carboxylic acid; m.p. 160°–165' (dec.).

In an analogous manner, by employing L-2-thienylglycine for the D-isomer in part (a), one obtains 7β-[[L-[(aminocarbonyl)amino]-2-thienylacetyl]amino]-3-[[4-(aminocarbonyl)pyridino]methyl]-8-oxo-5-thia-1-azabicyclo[4.2.0]-oct-2-ene-2-carboxylic acid.

EXAMPLE 2

7α-Methoxy-7β-[[D-[(aminocarbonyl)amino]-2-thienylacetyl]-amino]-3-[[4-aminocarbonyl)pyridino]-methyl]-8-oxo-5-thia-1-azabicyclo[4.2.0]oct-2-ene-2-carboxylic acid (a) 3-[(Acetyloxy)methyl]-7α-methoxy-7β-[[D-[[[(4-methoxyphenyl)-methoxy]carbonyl]amino]-2-thienylacetyl]amino]-8-oxo-5-thia-1-azabicyclo[4.2.-0]oct-2-ene-2-carboxylic acid, diphenylmethyl ester 3.2 g. (0.01 mol.) of the product from example 1(a) is brought into solution in 40 ml. of methylene chloride with 1.1 ml. of N-methylmorpholine. The solution is cooled to −15°, 1.39 ml. of isobutylchloroformate are added, and the mixture is stirred for 10 minutes. To this is added a solution of 4.7 g. (0.01 mol.) of 7β-amino-7α-methoxy cephalosporanic acid diphenylmethyl ester and 3.1 ml. of triethylamine in 40 ml. of methylene chloride. The mixture is stirred for 1 hour at −5° and 1 hour at 5°. This mixture is then evaporated to dryness in a rotary evaporator and the solid residue is triturated with ether and filtered under suction to yield the titled compound.

(b) 3-[(Acetyloy)methyl]-7α-methoxy-7β-[D-2-amino-2-(2-thienyl)-acetamido]-8-oxo-5-thia-1-azabicyclo[4.2.0]oct-2-ene-2-carboxylic acid The product from part (a) is trated with trifluoroacetic acid and anisole according to the procedure of example 1(c) to yield 3-[(acetyloxy)methyl]-7α-methoxy-7β-[D-2-amino-2-(2-thienyl)-acetamido]-8-oxo-5-thia-1-azabicyclo[4.2.0]oct-2-carboxylic acid.

(c) 3-[(Acetyloxy)methyl]-7α-methoxy-7β-[[D-[(aminocarbonyl)-amino]-2-thienylacetyl]amino]-8-oxo-5-thia-1-azabicyclo-[4.2.0]oct-2-ene-2-carboxylic acid, sodium salt The product from part (b) is reacted with potassium cyanate according to the procedure of example 1(d) to yield 3-[(acetyloxy)methyl]-7α-methoxy-7β-[[D-[(aminocarbonyl)amino]-2-thienylacetyl]amino]-8-oxo-5-thia-1-azabicyclo[4.2.0]oct-2-ene-2-carboxylic acid.

An aqueous equimolar solution of this acid and sodium bicarbonate is lyophilized to yield 3-[(acetyloxy)-methyl]-7α-methoxy-7β-[[D-[(aminocarbonyl)amino]-2-thienylacetyl]amino]-8-oxo-5-thia-1-azabicyclo[4.2.0]oct-2-ene-2-carboxylic acid, sodium salt.

(d) 7α-Methoxy-7β-[[D-[(aminocarbonyl)amino]-2-thienylacetyl]-amino]-3-[[4-(aminocarbonyl)pyridino]-methyl]-8-oxo-5-thia-1-azabicyclo[4.2.0]oct-2-ene-2-carboxylic acid The sodium salt from part (c), 4-pyridinecarboxamide, potassium thiocyanate and water are reacted according to the procedure of example 1(e) to yield 7α-methoxy-7β-[[D-[(aminocarbonyl)amino]-2-thienylacetyl]amino]-3-[[4-(aminocarbonyl)-pyridino]-methyl]-8-oxo-5-thia-1-azabicyclo[4.2.0]oct-2-ene-2-carboxylic acid.

In an analogous manner, one can obtain 7α-methoxy-7β-[[L-[(aminocarbonyl)amino]-2-thienylacetyl-]amino]-3-[[4-(aminocarbonyl]pyridino]methyl]-8-oxo-5-thia-1-azabicyclo[4.2.0]oct-2-ene-2-carboxylic acid.

EXAMPLE 3

7β-[[D-[(Aminocarbonyl)amino]phenylacetyl]amino]-3-[[4-(aminocarbonyl) pyridino]methyl]-8-oxo-5-thia-1-azabicyclo[4.2.0]oct-2-ene-2-carboxylic acid, hydrate (a) D-2-[[[(4-Methoxyphenyl)methoxy]carbonyl-]amino]phenylacetic acid D-Phenylglycine and magnesium oxide are suspended in water and reacted with p-methoxybenzyloxycarbonylazide according to the procedure of example 1(a) to yield D-2-[[[(4-methoxyphenyl)-methoxy]carbonyl]amino]phenylacetic acid.

(b) 3-[(Acetyloxy)methyl]-7β-[D-2-amino-2-phenylacetamido]-8-oxo-5-thia-1-azabicyclo[4.2.0]oct-2-ene-2-carboxylic acid The product from part (a) and 7-aminocephalosporanic acid are reacted according to the procedure of example 1(b) to yield 3-[(acetyloxy)methyl]-7β-[[D-[[[(4-methoxyphenyl)-methoxy]carbonyl]amino]-phenylacetyl]amino]-8-oxo-5-thia-1-azabicyclo [4.2.0]oct-2-ene-2-carboxylic acid.

This compound is then treated with trifluoroacetic acid and anisole according to the procedure of example 1(c) to yield 3-[(acetyloxy)methyl]-7β-[[D-2-amino-2-phenylacetamido]-8-oxo-5-thia-1-azabicyclo [4.2.0]oct-2-ene-2-carboxylic acid.

(c) 3-[(Acetyloxy)methyl]-7β-[[D-[(aminocarbonyl-)amino]phenylacetyl]amino]-8-oxo-5-thia-1-azabicyclo[4.2.0] oct-2-ene-2-carboxylic acid, sodium salt The product from part (b) is reacted with potassium cyanate according to the procedure of example 1(d) to yield 3-[(acetyloxy)methyl]-7β-[[D-[(aminocarbonyl-)amino]phenylacetyl]amino]-8-oxo-5-thia-1-azabicyclo[4.2.0]oct-2-ene-2-carboxylic acid.

An aqueous equimolar solution of this acid and sodium bicarbonate is lyophilized to yield the sodium salt.

(d) 7β-[[D-[(Aminocarbonyl)amino]phenylacetyl-]amino]-3-[[4-(aminocarbonyl)pyridino]methyl]-8-oxo-5-thia-1-azabicyclo-[4.2.0]oct-2-ene-2-carboxylic acid, hydrate A mixture of 1.88 g. (0.004 mole) of the sodium salt product from part (c), 0.732 g. (0.006 mole) of 4-pyridine-carboxamide, 9.6 g. of potassium thiocyanate and 6 ml. of water is heated at 150° for 24 hours. A clear solution is obtained. A chromatography column is filled with 70 g. of ion exchange resin Amberlite XAD-2. The reaction solution is diluted with 30 ml. of water and is admixed with 200 g. of a paste of ion exchange resin Amberlite XAD-2-. This mixture is stirred for 30 minutes and added to the chromatography column containing the 70 g. of ion exchange resin. The column is then eluted with 30 ml. portions of water. After 120 fractions are collected, the column is eluted with a mixture of water and methanol (80:20) and 10 ml. fractions are collected. The eluate is subjected to thin layer chromatography and checked for the content of the desired product. Fractions 45–120 of the water-methanol eluate are combined and concentrated to about 150 ml. to yield as crystals 160 mg. of 7β-[[D-[(aminocarbonyl)amino]-phenylacetyl]amino]-3-[[4-(aminocarbonyl) pyridino]-methyl]-8-oxo-5-thia-1-azabicyclo [4.2.0]oct-2-ene-2-carboxylic acid, hydrate; m.p. 187°–190° (dec.). An additional 280 mg. of not so pure methanol are obtained from the mother liquor. Fractions 121–160 of the water-methanol eluate are concentrated to about 50 ml. and lyophilized to obtain an additional 100 mg. of the desired product; m.p. 177°–185° (dec.).

In an analogous manner, by employing L-phenylglycine in part (a), one obtains 7β-[[L-[(aminocarbonyl-)amino]phenylacetyl]amino]-3-[[4-aminocarbonyl)-pyridino]methyl]-8-oxo-5-thia-1-azabicyclo[4.2.0]oct-2-ene-2-carboxylic acid, hydrate.

EXAMPLES 4–25

Following the procedure of examples 1–3 but employing the acylating agent shown in Col. I and the 7α-methoxy or desmethoxy-7β-amino-cephalosporanic acid (or its diphenylmethyl ester) shown in Col. II one obtains the intermediate of Col. III (or its diphenylmethyl ester). The protecting group (and ester group) are removed by treatment with trifluoroacetic acid and anisole. Treatment of the resulting trifluoroacetic acid salt with potassium cyanate yields the acid of Col. IV. The acid of Col. IV in converted to its sodium salt and reacted with the carbamoyl substituted pyridine of Col. V to yield the final product of Col. VI.

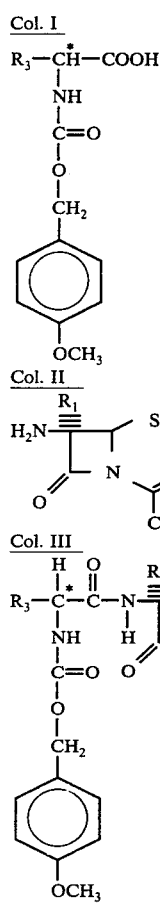
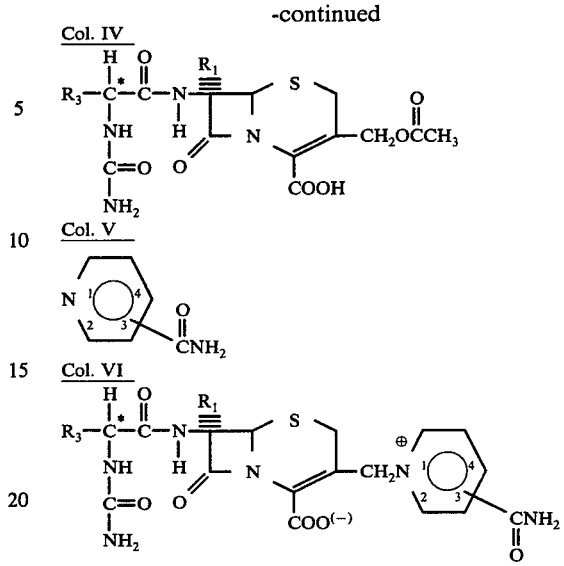
| Ex. | $R_3$ | $R_1$ | position on pyridinium-carboxamide |
|---|---|---|---|
| 4 | (thienyl) | —H | 4 |
| 5 | (3-chlorothienyl) | —H | 3 |
| 6 | (5-methylthienyl) | —OCH$_3$ | 4 |
| 7 | (furyl) | —H | 2 |
| 8 | (furyl) | —OCH$_3$ | 4 |
| 9 | (pyridyl) | —H | 4 |
| 10 | (6-chloropyridyl) | —OCH$_3$ | 3 |

-continued
| Ex. | R₃ | R₁ | 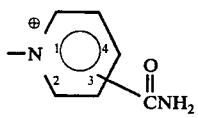 |
|---|---|---|---|
| 11 | (pyridyl) | —H | 2 |
| 12 | (phenyl) | —OCH₃ | 4 |
| 13 | (4-hydroxyphenyl) | H | 4 |
| 14 | (4-hydroxyphenyl) | —OCH₃ | 4 |
| 15 | (3,5-dichlorophenyl) | —H | 2 |
| 16 | (4-methoxybenzyl) H₃CO—C₆H₄—CH₂— | —OCH₃ | 4 |
| 17 | (benzyl) —CH₂— | —H | 4 |
| 18 | (4-methylbenzyl) H₃C—C₆H₄—CH₂— | —H | 3 |
| 19 | (cyclohexenyl) | —H | 4 |
| 20 | (cyclohexenyl) | —OCH₃ | 4 |
| 21 | (cyclohexenyl) | —H | 3 |
| 22 | (thienyl) | —OCH₃ | 4 |
| 23 | H— | —H | 4 |
| 24 | —C₂H₅ | —OCH₃ | 4 |
| 25 | (cyclohexyl) | —H | 4 |
The acylating agents of Col. I may be in either the D- or L- form or may be a mixture of D- and L-isomers.

7β-[[D-[Methylaminocarbonyl)amino]-2-thienylacetyl-]amino]-3-[[4-(aminocarbonyl)pyridino]methyl]-8-oxo-5-thia-1-azabicyclo-[4.2.0]oct-2-ene-2-carboxylic acid (a) 3-[(Acetyloxy)methyl]-7β-[[D-[(methylaminocarbonyl)amino]-2-thienylacetyl]amino]-8-oxo-5-thia-1-azabicyclo[4.2.0]oct-2-ene-2-carboxylic acid, sodium salt 1.5 g. of 3-[(acetyloxy)methyl]-7β-[D-2-amino-2-(2-thienyl)acetamido]-8-oxo-5-thia-1-azabicyclo[4.2.0]oct-2-ene-2carboxylic acid, trifluoroacetic acid salt from example 1(c) and 1.01 ml. of triethylamine are dissolved at 0°–5° in 20 ml. of anhydrous methylene chloride. To the clear solution is added 2.49 g. of a 10% solution of methylisocyanate in methylene chloride. This mixture is stirred for 2 hours at 0°–5° and then concentrated. The residue is taken up in a little water, shaken with ether, filtered and acidified with 2N hydrochloric acid to yield 3-[(acetyloxy)methyl]-7β-[[D-[(methylaminocarbonyl)amino]-2-thienylacetyl]amino]-8-oxo-5-thia-1-azabicyclo [4.2.0]oct-2-ene-2-carboxylic acid.

An aqueous equimolar solution of this acid and sodium bicarbonate is lyophilized to yield 3-[(acetyloxy)methyl]-7β-[[D-[(methylaminocarbonyl)amino]-2-thienylacetyl]amino]-8-oxo-5-thia-1-azabicyclo[4.2.0]oct-2-ene-2-carboxylic acid, sodium salt.

(b) 7β-[[D-[(Methylaminocarbonyl)amino]-2-thienylacetyl]amino]-3-[[4-(aminocarbonyl)pyridino]methyl]-8-oxo-5-thia-1-azabicyclo[4.2.0]oct-2-ene-2-carboxylic acid The sodium salt product from part (a) is reacted with 4-pyridinecarboxamide, potassium thiocyanate and water according to the procedure of example 1(e) to yield 7β-[[D-[(methylaminocarbonyl)amino]-2-thienylacetyl]amino]-3-[[4-(aminocarbonyl)-pyridino]methyl]-8-oxo-5-thia-1-azabicyclo[4.2.0]oct-2-ene-2-carboxylic acid.

In an analogous manner, one can obtain 7β-[[L-[(methyl-aminocarbonyl)amino]-2-thienylacetyl-]amino]-3-[[4-(aminocarbonyl)-pyridino]methyl]-8-oxo-5-thia-1-azabicyclo[4.2.0]oct-2-ene-2-carboxylic acid.

EXAMPLES 27–33

Following the procedure of example 26 but substituting for the methylisocyanate one of the following:
ethylisocyanate
n-propylisocyanate
i-propylisocyanate
n-butylisocyanate
i-butylisocyanate
t-butylisocyanate
n-pentylisocyanate
one obtains:

7β-[[D-[(ethylaminocarbonyl)amino]-2-thienylacetyl]-amino]-3-[[4-(aminocarbonyl)pyridino]methyl]-8-oxo-5-thia-1-azabicyclo[4.2.0]oct-2-ene-2-carboxylic acid;

7β-[[D-[(n-propylaminocarbonyl)amino]-2-thienylacetyl]-amino]-3-[[4-(aminocarbonyl)pyridino]methyl]-8-oxo-5-thia-1-azabicyclo[4.2.0]oct-2-ene-2-carboxylic acid;

7β-[[D-[(i-propylaminocarbonyl)amino]-2-thienylacetyl]-amino]-3-[[4-(aminocarbonyl)pyridino]methyl]-8-oxo-5-thia-1-azabicyclo[4.2.0]oct-2-ene-2-carboxylic acid;

7β-[[D-[n-butylaminocarbonyl)amino]-2-thienylacetyl]-amino]-3-[[4-(aminocarbonyl)pyridino]methyl]-8-oxo-5-thia-1-azabicyclo[4.2.0]oct-2-ene-2-carboxylic acid;

7β-[[D-[(i-butylaminocarbonyl)amino]-2-thienylacetyl]-amino]-3-[[4-(aminocarbonyl)pyridino]methyl]-8-oxo-5-thia-1-azabicyclo[4.2.0]oct-2-ene-2-carboxylic acid;

7β-[[D-[(t-butylaminocarbonyl)amino]-2-thienylacetyl]-amino]-3-[[4-(aminocarbonyl)pyridino]methyl]-8-oxo-5-thia-1-azabicyclo[4.2.0]oct-2-ene-2-carboxylic acid; and 7β-[[D-[(n-pentylaminocarbonyl)amino]-2-thienylacetyl]-amino]-3-[[4-(aminocarbonyl)pyridino]methyl]-8-oxo-5-thia-1-azabicyclo[4.2.0]oct-2-ene-2-carboxylic acid; respectively.

In an analogous manner, one can obtain the L-isomers of the compounds of examples 27 and 33.

Similarly, by employing the methylisocyanate from example 26 or the alkylisocyanates of examples 27–33 in the procedure of examples 2 to 25, other compounds within the scope of this invention are obtained.

What is claimed is:

1. A compound of the formula:

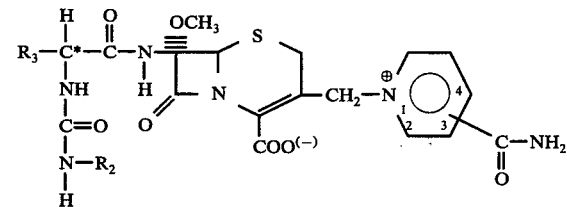

wherein the 7α-methoxy substituent is in the α-configuration; $R_2$ is hydrogen or lower alkyl; $R_3$ is hydrogen, lower alkyl, cycloalkyl of 3 to 7 carbons, cycloalkenyl of 3 to 7 carbons, cycloalkadienyl of 6 or 7 carbons, phenyl, phenyl-lower alkyl, substituted phenyl or phenyl-lower alkyl wherein said phenyl substituent is one or two members selected from the group consisting of halogen, lower alkyl of 1 to 4 carbons, lower alkoxy of 1 to 4 carbons, and hydroxy, or a mono-substituted or unsubstituted heterocyclic selected from the group consisting of 2-thienyl, 3-thienyl, 2-furyl, 3-furyl, 2-pyridyl, 3-pyridyl, and 4-pyridyl wherein said heterocyclic substituent is attached at an available carbon atom and is halogen or lower alkyl of 1 to 4 carbons; and the

substituent is in 2-, or 3- or 4-position.

2. The compound of claim 1 wherein $R_2$ is hydrogen or straight or branched chain alkyl of 1 to 8 carbons; and $R_3$ is cycloalkadienyl of 6 or 7 carbons, cycloalkenyl of 6 or 7 carbons, phenyl, benzyl, phenethyl, substituted phenyl, benzyl or phenethyl wherein said substituent is on the phenyl ring and is one or two members selected from the group consisting of chloro, bromo, methyl, ethyl, methoxy, ethoxy and hydroxy, or a mono-substituted or unsubstituted heterocyclic selected from the group consisting of 2-thienyl, 3-thienyl, 2-furyl, 3-furyl, 2-pyridyl, 3-pyridyl, and 4-pyridyl wherein said heterocyclic substituent is attached at an available carbon atom and is chloro, bromo, methyl, or ethyl.

3. The compound of claim 2 wherein $R_2$ is hydrogen.

4. The compound of claim 3 wherein $R_3$ is 2-thienyl, 3-thienyl, phenyl or 4-hydroxyphenyl; and the

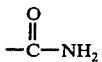

substituent is in the 4-position.

5. The compound of claim 4 wherein $R_3$ is 2-thienyl.
6. The compound of claim 4 wherein $R_3$ is 3-thienyl.
7. The compound of claim 4 wherein $R_3$ is phenyl.
8. The compound of claim 4 wherein $R_3$ is 4-hydroxyphenyl.
9. The compound of claim 2 wherein $R_2$ is straight or branched chain alkyl of 1 to 8 carbons.
10. The compound of claim 9 wherein $R_2$ is straight or branched chain alkyl of 1 to 4 carbons; $R_3$ is 2-thienyl, 3-thienyl, phenyl or 4-hydroxyphenyl; and the

substituent is in the 4-position.

11. The compound of claim 10 wherein $R_3$ is 2-thienyl.
12. The compound of claim 11 wherein $R_2$ is methyl.
13. The compound of claim 10 wherein $R_3$ is 3-thienyl.
14. The compound of claim 13 wherein $R_2$ is methyl.
15. The compound of claim 10 wherein $R_3$ is phenyl.
16. The compound of claim 15 wherein $R_2$ is methyl.
17. The compound of claim 10 wherein $R_3$ is 4-hydroxyphenyl.
18. The compound of claim 17 wherein $R_2$ is methyl.

* * * * *

UNITED STATES PATENT AND TRADEMARK OFFICE
CERTIFICATE OF CORRECTION

PATENT NO. : 4,100,345
DATED : July 11, 1978
INVENTOR(S) : Hermann Breuer et al.

It is certified that error appears in the above-identified patent and that said Letters Patent are hereby corrected as shown below:

Col. 7, line 13, "trated" should read -- treated --.

Col. 7, line 31, ".0oct" should read -- .0]oct --.

Signed and Sealed this

Nineteenth Day of December 1978

[SEAL]

Attest:

RUTH C. MASON
Attesting Officer

DONALD W. BANNER
Commissioner of Patents and Trademarks